(12) United States Patent
Park et al.

(10) Patent No.: US 9,977,509 B2
(45) Date of Patent: May 22, 2018

(54) GESTURE RECOGNITION METHOD, APPARATUS AND WEARABLE DEVICE

(71) Applicant: Samsung Electronics Co., Ltd., Suwon-si (KR)

(72) Inventors: Chang Soon Park, Chungju-si (KR); Ui Kun Kwon, Hwaseong-si (KR); Sang Joon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 5 days.

(21) Appl. No.: 15/186,796

(22) Filed: Jun. 20, 2016

(65) Prior Publication Data

US 2017/0147077 A1    May 25, 2017

(30) Foreign Application Priority Data

Nov. 20, 2015  (KR) .................. 10-2015-0163211

(51) Int. Cl.
| | |
|---|---|
| *G06F 3/01* | (2006.01) |
| *G06F 1/16* | (2006.01) |
| *A61B 5/024* | (2006.01) |
| *A61B 5/0402* | (2006.01) |
| *G06F 21/32* | (2013.01) |
| *G08C 17/02* | (2006.01) |

(52) U.S. Cl.
CPC .......... *G06F 3/017* (2013.01); *A61B 5/02416* (2013.01); *A61B 5/0402* (2013.01); *G06F 1/163* (2013.01); *G06F 3/011* (2013.01); *G06F 21/32* (2013.01); *G08C 17/02* (2013.01)

(58) Field of Classification Search
CPC .......... G06F 3/017; G06F 3/011; G06F 1/163; G06F 21/32; A61B 5/02416; A61B 5/0402; G08C 17/02
See application file for complete search history.

(56) References Cited

U.S. PATENT DOCUMENTS

| | | | | |
|---|---|---|---|---|
| 6,238,338 | B1 * | 5/2001 | DeLuca | A61B 5/681 128/903 |
| 6,244,873 | B1 * | 6/2001 | Hill | G06F 3/015 379/110.01 |
| 9,327,398 | B2 * | 5/2016 | Sankai | B25J 9/0006 |

(Continued)

FOREIGN PATENT DOCUMENTS

| | | |
|---|---|---|
| CN | 104699242 A | 6/2015 |
| JP | 2015-122023 A | 7/2015 |

(Continued)

OTHER PUBLICATIONS

European Search Report dated Apr. 19, 2017 in corresponding European Patent Application No. 16198885.2 (11 pages in English).

*Primary Examiner* — Tom Sheng
(74) *Attorney, Agent, or Firm* — NSIP Law

(57) ABSTRACT

A method and an apparatus for gesture recognition and a wearable device for gesture recognition are described. A method of gesture recognition involves using a processor to detect a motion artifact from an output signal of a biosignal sensor and generating a control signal to control a function of a target device that corresponds to a reference signal pattern in response to a signal pattern of the detected motion artifact corresponding to the reference signal pattern.

20 Claims, 13 Drawing Sheets

(56) References Cited

U.S. PATENT DOCUMENTS

| | | | |
|---|---|---|---|
| 2003/0046254 A1* | 3/2003 | Ryu | A61F 4/00 706/15 |
| 2008/0303788 A1* | 12/2008 | Kurashima | G06F 3/014 345/156 |
| 2009/0005699 A1* | 1/2009 | Sakurai | A61B 5/0488 600/546 |
| 2009/0082829 A1* | 3/2009 | Panken | A61N 1/36139 607/45 |
| 2011/0004118 A1* | 1/2011 | Wheeler | A61N 1/36003 600/546 |
| 2011/0264008 A1* | 10/2011 | Yang | A61B 5/0488 600/595 |
| 2013/0046157 A1* | 2/2013 | Addison | A61B 5/0002 600/323 |
| 2013/0265229 A1 | 10/2013 | Forutanpour et al. | |
| 2014/0297218 A1 | 10/2014 | Yuen | |
| 2014/0368474 A1 | 12/2014 | Kim et al. | |
| 2015/0065841 A1* | 3/2015 | Lee | A61B 5/053 600/388 |
| 2015/0065842 A1* | 3/2015 | Lee | A61B 5/04085 600/388 |
| 2015/0074797 A1* | 3/2015 | Choi | G06F 21/32 726/19 |
| 2015/0149116 A1* | 5/2015 | Cho | G01G 9/00 702/173 |
| 2016/0007876 A1* | 1/2016 | Yoshioka | A61B 5/0492 600/384 |
| 2016/0007926 A1* | 1/2016 | Kang | A61B 5/721 600/301 |
| 2016/0314781 A1* | 10/2016 | Schultz | A61B 5/04886 |

FOREIGN PATENT DOCUMENTS

| | | |
|---|---|---|
| KR | 10-2014-0113118 A | 9/2014 |
| KR | 10-2015-0027876 A | 3/2015 |
| KR | 10-2015-0060553 A | 6/2015 |
| KR | 10-2015-0077684 A | 7/2015 |
| KR | 10-2015-0082079 A | 7/2015 |
| KR | 10-2015-0088599 A | 8/2015 |

* cited by examiner

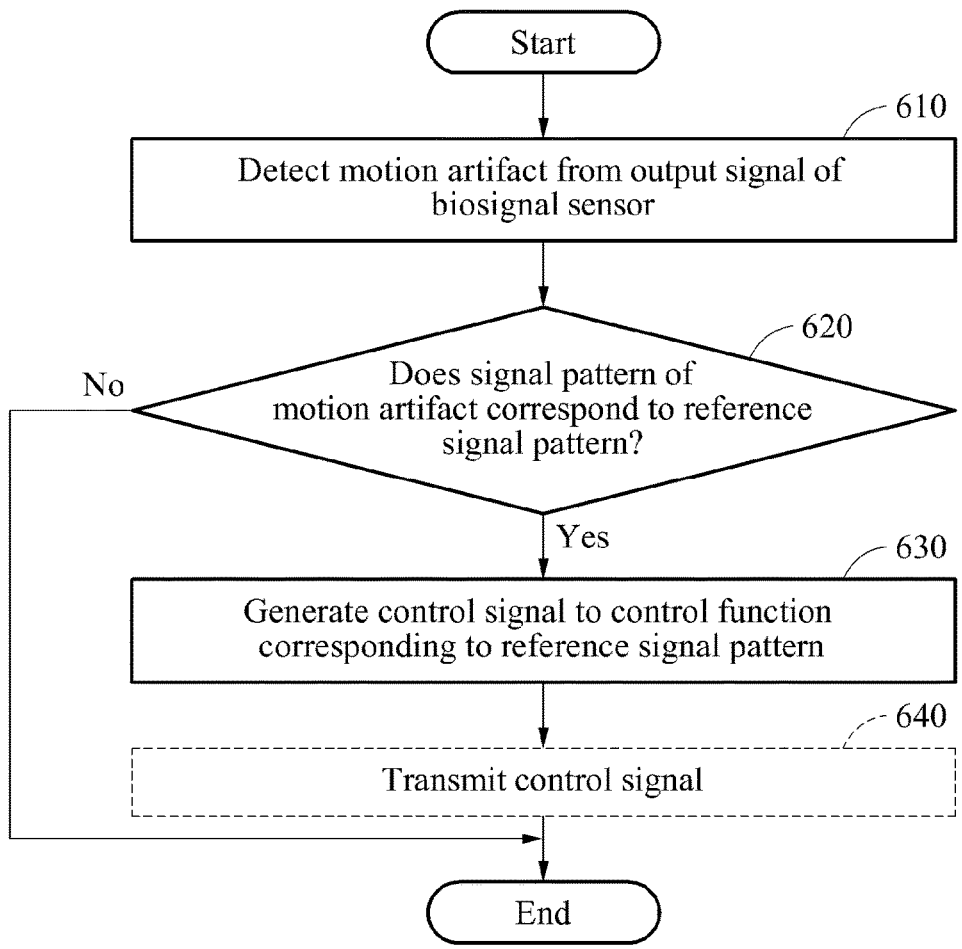

GESTURE RECOGNITION METHOD, APPARATUS AND WEARABLE DEVICE

CROSS-REFERENCE TO RELATED APPLICATION(S)

This application claims the benefit under 35 USC 119(a) of Korean Patent Application No. 10-2015-0163211 filed on Nov. 20, 2015, in the Korean Intellectual Property Office, the entire disclosure of which is incorporated herein by reference for all purposes.

BACKGROUND

1. Field

The following description relates to a method and an apparatus for gesture recognition, and a wearable device for gesture recognition.

2. Description of Related Art

Gesture recognition technology is used to enable devices to recognize different gestures of a user and to respond to that detected gesture as a control command. For example, a device may be able to identify a gesture by tracking the movement of an entire body or a portion of the body of the user, such as a torso, a hand, a face and the like of the user. Based on the recognized movement, the device may control a function of the device. Examples of the gesture recognition technology includes a method of detecting a change in an electronic signal generated by muscles using an electromyogram (EMG) sensor and estimating a gesture performed by a user based on the detected change, and a method of measuring an inertia from a physical movement of a user using a motion sensor such as an accelerometer and a gyroscope and estimating a gesture performed by the user based on the measured inertia.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a gesture recognition method involves detecting, using a processor, a motion artifact from an output signal of a biosignal sensor; and generating a control signal to control a function of a target device that corresponds to a reference signal pattern in response to a signal pattern of the detected motion artifact corresponding to the reference signal pattern.

The generating of the control signal may involve determining a type of a gesture performed by a user based on the signal pattern of the motion artifact and at least one reference signal pattern stored in a memory, and generating the control signal to operate the target device based on the determined type of the gesture.

The motion artifact may occur by a physical pressure or a movement applied by a user to the biosignal sensor or an area in a vicinity of the biosignal sensor.

The general aspect of the method may further involve, in response to the motion artifact not being detected from the output signal, estimating health information of a user based on a biosignal detected from the output signal.

The generating of the control signal may involve performing a user authentication based on a biosignal detected from the output signal and generating the control signal in response to a successful user authentication.

The generating of the control signal may involve determining presence or absence of the reference signal pattern corresponding to the signal pattern of the motion artifact among pre-registered reference signal patterns.

The reference signal pattern may be generated by determining a function type by a user selecting the function type and registering a signal pattern of a motion artifact corresponding to the determined function type.

The biosignal sensor may be included in a wearable device. The generating of the control signal to control the function of the target device comprises controlling a function of the wearable device or a function of another device connected to the wearable device.

The other device may be one of a mobile terminal, an Internet of things (IoT) device, and a smart vehicle.

The detecting of the motion artifact may involve determining whether the motion artifact occurs based on a mean value of the output signal in a time interval.

The general aspect of the method may further involve wirelessly transmitting the control signal to a device performing the function.

The biosignal sensor may be configured to measure a biosignal including at least one of a photoplethysmogram (PPG) signal and an electrocardiogram (ECG) signal, the biosignal being associated with a health condition of a user.

In another general aspect, a non-transitory computer-readable storage medium may store instructions that, when executed, cause computing hardware to perform the general aspect of the method described above.

In another general aspect, a gesture recognition apparatus includes at least one processor, and at least one memory configured to store instructions to be executed by the processor. The instructions, when executed, cause the processor to detect a motion artifact from an output signal of a biosignal sensor, and generate a control signal to control a function of a target device corresponding to a reference signal pattern in response to a signal pattern of the detected motion artifact corresponding to the reference signal pattern.

The biosignal sensor may be included in a wearable device, and the generating of the control signal may involve generating the control signal to control a function of the wearable device or a function of another device connected to the wearable device.

The generating of the control signal may involve determining presence or absence of the reference signal pattern corresponding to the signal pattern of the motion artifact among pre-registered reference signal patterns.

In another general aspect, a wearable device includes a biosignal sensor configured to measure a biosignal, a motion artifact processor configured to detect a motion artifact from an output signal of the biosignal sensor, a gesture recognition processor configured to generate a control signal to control a function corresponding to a reference signal pattern in response to a signal pattern of the detected motion artifact corresponding to the reference signal pattern, and a health information processor configured to determine health information of a user based on the biosignal.

The gesture recognition processor may be configured to determine a type of a gesture performed by the user based on the signal pattern of the motion artifact and at least one reference signal pattern, and generate the control signal to control a function corresponding to the determined type of the gesture.

In response to the motion artifact not being detected from the output signal of the biosignal sensor, the health information processor may be configured to determine the health information based on the output signal of the biosignal sensor.

The gesture recognition processor may be configured to perform a user authentication based on the biosignal and generate the control signal in response to a successful user authentication.

In another general aspect, a wearable device includes a biosignal sensor configured to measure a biosignal, and a motion artifact processor configured to determine whether a motion artifact is present in an output signal of the biosensor, and in response to a determination that a motion artifact is present, initiate a gesture type processor to determine whether the motion artifact corresponds to a reference signal, and in response to a determination that a motion artifact is not present, initiate a biosignal processor to process the output of the biosignal sensor to determine a health condition of a user.

The wearable device may not include an EMG sensor.

The biosignal sensor includes a PPG sensor.

The general aspect of the wearable device further includes a control signal generating circuit configured to generate a control signal based on the reference signal, and a transmitter configured to transmit the control signal to a device located apart from the wearable device.

Other features and aspects will be apparent from the following detailed description, the drawings, and the claims.

BRIEF DESCRIPTION OF THE DRAWINGS

FIG. 6 is a flowchart illustrating an example of a gesture recognition method.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
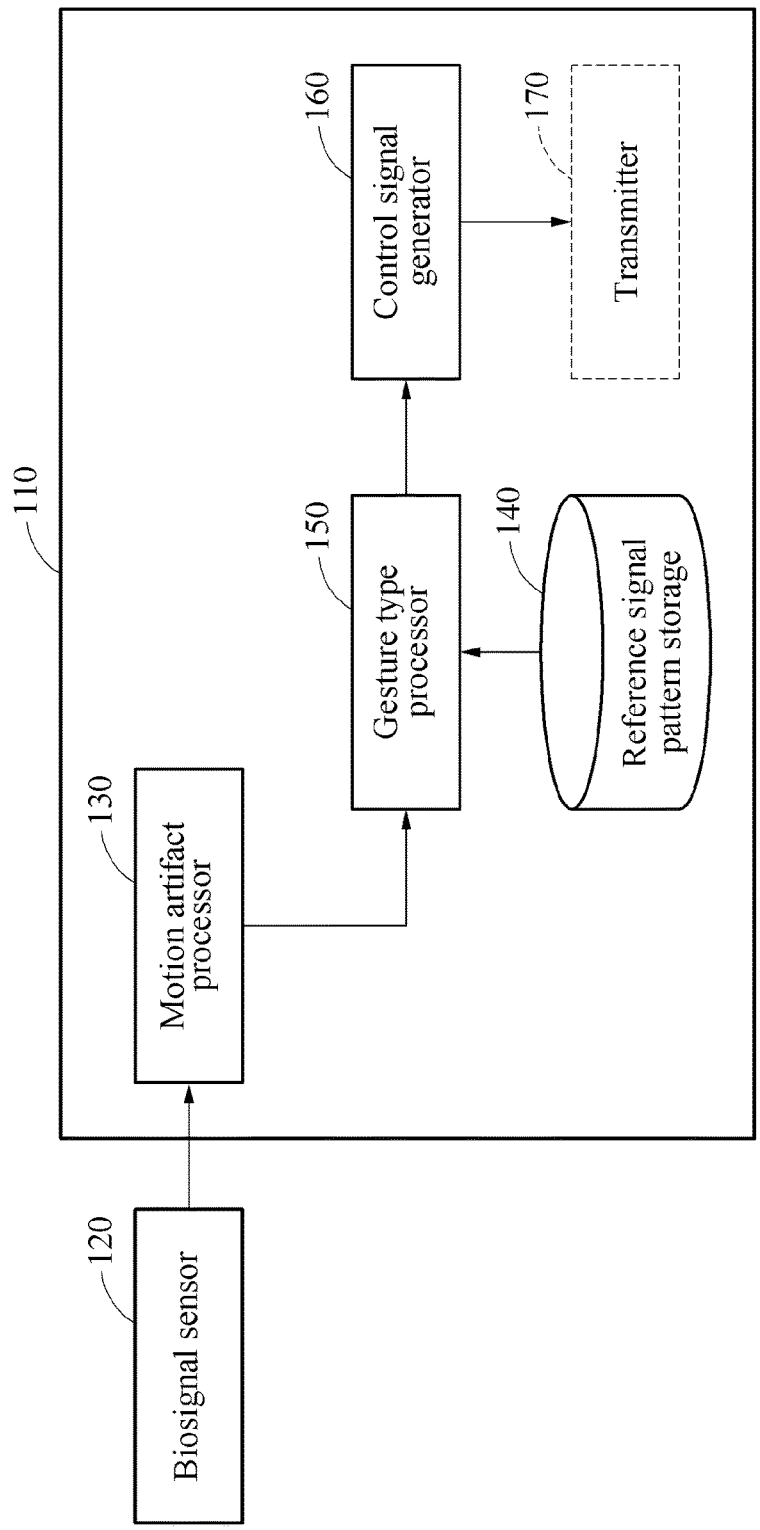
FIG. 1 is a diagram illustrating an example of a gesture recognition apparatus.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The terminology used herein is for the purpose of describing various examples only and is not intended to limit the disclosure. As used herein, the terms "a," "an," and "the" are intended to include the plural forms as well, unless the context clearly indicates otherwise. As used herein, the terms "comprises," "comprising," "includes," "including," "has," and "having" specify the presence of stated features, numbers, operations, elements, components, and combinations thereof, but do not preclude the presence or addition of one or more other features, numbers, operations, elements, components, and combinations thereof.

In addition, terms such as first, second, A, B, (a), (b), and the like may be used herein to describe components. Each of these terminologies is not used to define an essence, order or sequence of a corresponding component but used merely to distinguish the corresponding component from other component(s).

Examples to be described hereinafter may be applicable to a technology for recognizing a gesture performed by a user and controlling a function of a device based on the recognized gesture. According to one example, when a user wearing a wearable device for gesture recognition performs a pre-registered gesture, a motion artifact that occurs in an output signal of a biosensor in the wearable device due to the gesture may be detected by a process of the wearable device. The gesture may be recognized based on a signal pattern of the detected motion artifact. As a result of the gesture recognition, the wearable device or another device connected to the wearable device may be controlled to perform a function predefined for each pre-registered gesture.

The wearable device may be provided in a form of, for example, a watch, a bracelet, a band, glasses, and a ring. The other device connected to the wearable device may include, for example, a mobile terminal, a smart home appliance, an Internet of things (IoT) device, and a smart vehicle. However, the types of devices are not limited to the aforementioned example. The mobile terminal may be, for example, a personal digital assistant (PDA), a smartphone, a tablet computer, and a laptop computer, which include a communication function. The smart home appliance may be, for example, a television (TV), a refrigerator, an audio system, an air-conditioner, a washing machine, a set-top box, and a vacuum cleaner. The IoT device may include all devices remotely controllable through the Internet.

Hereinafter, examples are described in detail with reference to the accompanying drawings. Like reference numerals in the drawings denote like elements, and a known function or configuration will be omitted herein.

FIG. 1 illustrates an example of a gesture recognition apparatus 110.

The gesture recognition apparatus 110 recognizes a gesture performed by a user. The gesture recognition apparatus 110 recognizes the gesture performed by the user based on an output signal of a biosignal sensor 120. The biosignal sensor 120 is configured to measure a biosignal of the user. According to one example, both the gesture recognition apparatus 110 and the biosignal sensor 120 may be included in a wearable device. However, the present description is not limited thereto; in another example, the gesture recognition apparatus 110 and the biosignal sensor 120 may be included in two separate devices. The gesture recognition apparatus 110 may recognize a gesture performed by the user based on a change in an output signal of the biosignal sensor 120 that occurs in response to the user wearing the wearable device performing a pre-defined gesture. A biosignal refers to a signal including bioinformation measured from a body of the user. Examples of a biosignal include, for example, a photoplethysmogram (PPG) signal and an electrocardiogram (ECG) signal. The PPG signal indicates a change in a vascular volume based on a change in a blood flow, and the ECG signal indicates a change in a displacement of a heart. Hereinafter, detailed operations of the gesture recognition apparatus 110 will be described with reference to FIG. 1.

Referring to FIG. 1, the gesture recognition apparatus 110 includes a motion artifact processor 130, a reference signal pattern storage 140, a gesture type processor 150, and a control signal generator 160. The motion artifact processor 130, gesture type processor 150, and control signal generator 160 may be implemented with one or more processors, circuits and memories. The reference signal pattern storage may include a memory storing reference signal patterns.

A user may perform a gesture in order to cause a pre-defined function to be executed, and a corresponding motion artifact may occur in an output signal of the biosignal sensor 120 due to the gesture performed by the user. The motion artifact refers to noise that occurs due to an intentional movement of the user while a biosignal is being measured from a body of the user by the biosignal sensor 120. A motion artifact may occur, not only by a movement of the user due to a muscular contraction and relaxation, but also by a physical pressure or a movement intentionally applied by the user to the biosignal sensor 120 or an area in the vicinity of the biosignal sensor 120. In response to the user performing a predefined gesture for gesture recognition, an intentional motion artifact may occur in the output signal of the biosignal sensor 120, and a signal pattern of the motion artifact may vary depending on a gesture performed by the user.

The motion artifact processor 130 detects the motion artifact from an output signal of the biosignal sensor 120. The motion artifact processor 130 determines whether the output signal of the biosignal sensor 120 indicates a biosignal measured from the body of the user or the motion artifact occurred by the gesture performed by the user. In response to an amplitude of the output signal of the biosignal sensor 120 being greater than or equal to a threshold value, the motion artifact processor 130 may determine that a motion artifact has occurred. The threshold value may be based on a mean value of the output signal of the biosignal sensor 120 during a time interval. For example, the threshold value may increase when the mean value of the output signal increases, and the threshold value may decrease when the mean value of the output signal decreases.

According to one example, the motion artifact processor 130 may sample the output signal of the biosignal sensor 120 based on a time interval, and determine a mean value of sampled signal values. The motion artifact processor 130 may determine a deviation between the determined mean value and an output signal value to be sampled. In response to a value of the deviation being greater than a preset threshold value, the motion artifact processor 130 may determine occurrence of the motion artifact in the output signal of the biosignal sensor 120.

In response to detecting the motion artifact in the output signal of the biosignal sensor 120, the gesture type processor 150 determines a type of the gesture performed by the user based on a signal pattern of the motion artifact and at least one pre-registered reference signal pattern. The signal pattern of the motion artifact may be based on a form, for example, a signal waveform of the motion artifact bulging upwardly or downwardly in a time interval in which the motion artifact occurs, and on the number of times of upward bulging or downward bulging of the signal waveform. In the event that a plurality of reference signal patterns are stored in the gesture recognition apparatus 110, the gesture type processor 150 determines the presence or absence of a reference signal pattern corresponding to the signal pattern of the motion artifact among the plurality of reference signal patterns. A gesture is predefined for each reference signal pattern, and the gesture type processor 150 determines the type of the gesture performed by the user by identifying the reference signal pattern corresponding to the signal pattern of the motion artifact.

A reference signal pattern is registered in an additional registration process, and a single reference signal pattern or a plurality of reference signal patterns may be registered based on the number of registered gestures. The registration process in which a reference signal pattern is registered in advance may involve determining a device what will be controlled and a function type to be controlled by the recognized gesture, and registering a signal pattern of a motion artifact corresponding to the determined device and the function type. By storing a signal pattern of a motion artifact that occurs in an output signal of the biosignal sensor 120 during the user performs a gesture to be registered, a reference signal pattern corresponding to a gesture may be registered. Information on the registered reference signal pattern may be stored in the reference signal pattern storage 140.

The gesture type processor 150 determines whether the signal pattern of the motion artifact corresponds to the reference signal pattern by comparing a feature of the signal pattern of the motion artifact to a feature of a pre-registered reference signal pattern. The feature of the signal pattern of the motion artifact may be based on a signal waveform of the motion artifact and a signal feature point of the motion artifact, for example, a peak point, a maximum point, and a minimum point. For example, in response to a similarity between the signal waveform of the motion artifact and a waveform of the reference signal pattern being greater than or equal to a threshold value, the gesture type processor 150 may determine that the signal pattern of the motion artifact corresponds to the reference signal pattern. For another example, the gesture type processor 150 may determine, to be the reference signal pattern corresponding to the signal pattern of the motion artifact, a reference signal pattern having the number of peak points equal to the number of peak points greater than or equal to a threshold value in the signal waveform of the motion artifact.

The control signal generator 160 generates a control signal to control a function corresponding to the gesture determined by the gesture type processor 150. The control signal generator 160 may include a control signal generating circuit for generating the control signal. The control signal refers to a signal used to control a function that is predefined in a device, and the function to be controlled by the control signal may be selected by the user in the registration process.

The gesture recognition apparatus 110 may further include a transmitter 170 configured to wirelessly transmit the control signal generated by the control signal generator 160 to a target device to be controlled. For example, in response to the target device to be controlled being located apart from the gesture recognition apparatus 110, the transmitter 170 may wirelessly transmit the control signal to the target device. In this example, the control signal may be configured in a form of a packet, and address information of the target device and information on a function to be controlled may be included in a payload of the packet.

As described above, the gesture recognition apparatus 110 may recognize a gesture based on a change in an output signal of the biosignal sensor 120 configured to measure a biosignal without using an additional sensor, for example, an electromyogram (EMG) sensor and a motion sensor to recognize the gesture. In other words, the gesture recognition apparatus 110 according to one example may be implemented without using an EMG sensor. Thus, an amount of power consumption may be reduced and a cost for production may be reduced without using such an additional sensor for gesture recognition. For example, in the event that an EMG sensor is used for gesture recognition, the EMG sensor may need to be attached to skin to detect a muscular movement. However, according to an example, the gesture recognition technology may be performed using a PPG sensor that does not need to be attached to the skin, thereby increasing the convenience of the user. In addition, gesture recognition may be more intuitively performed in comparison to the gesture recognition performed using the EMG sensor configured to sense a fine electrical change of a muscle.

Further, because a gesture recognition that uses an EMG sensor or a motion sensor is performed by detecting a muscular movement or a movement of a device, a gesture may be incorrectly recognized or misrecognized in response to a user performing an unintentional gesture. However, according to an example, in the gesture recognition method using a motion artifact that occurs when a user intentionally moves a biosignal sensor or applies a physical pressure to an area in the vicinity of the biosignal sensor, a probability of incorrectly recognizing or misrecognizing an unintentional gesture performed by the user may be reduced.

Figure 2:
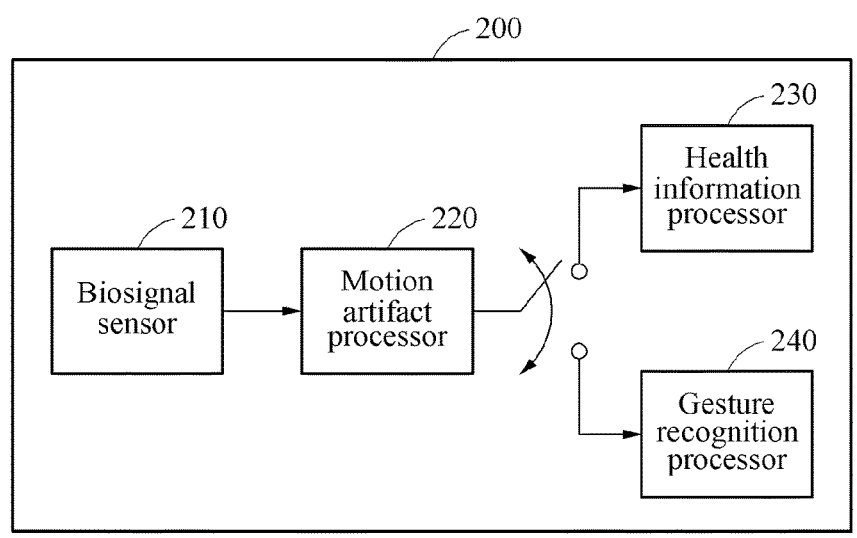
FIGS. 2 and 3 are diagrams illustrating an example of a wearable device.

FIG. 2 is a diagram illustrating an example of a wearable device 200.

The wearable device 200 monitors a health condition of a user, and conveniently controls a function of a device present in an area in the vicinity of the wearable device 200 through gesture recognition. The wearable device 200 determines health information of the user based on a biosignal measured by a biosignal sensor 210, for example, a PPG signal and an ECG signal, or recognizes a gesture performed by the user based on a motion artifact that occurs in an output signal of the biosignal sensor 210.

Referring to FIG. 2, the wearable device 200 includes the biosignal sensor 210, a motion artifact processor 220, a health information processor 230, and a gesture recognition processor 240.

The motion artifact processor 220 detects a motion artifact from an output signal of the biosignal sensor 210. The description of the motion artifact processor 130 illustrated in FIG. 1 may be applicable to the motion artifact processor 220 illustrated in FIG. 2, and thus a more detailed description will be omitted here. In response to not detecting the presence of any motion artifact in the output signal of the biosignal sensor 210, the motion artifact processor 220 may transfer a biosignal, which is the output signal of the biosignal sensor 210, to the health information processor 230. In response to detecting a motion artifact from the output signal of the biosignal sensor 210, the motion artifact processor 220 may transfer the output signal of the biosignal sensor 210 to the gesture recognition processor 240.

The health information processor 230 determines the health information of the user based on the biosignal measured by the biosignal sensor 210. In an example, in response to the biosignal sensor 210 measuring a PPG signal, the health information processor 230 may estimate cardiovascular information, for example, a blood pressure, based on the measured PPG signal. When the biosignal sensor 210 measures an ECG signal, the health information processor 230 may estimate heart disease information based on the measured ECG signal.

The gesture recognition processor 240 recognizes a gesture performed by the user based on a signal pattern of the motion artifact detected by the motion artifact processor 220. The gesture recognition processor 240 estimates a type of the gesture performed by the user by comparing the signal pattern of the motion artifact to a reference signal pattern, and generates a control signal to control a function corresponding to the gesture performed by the user.

Figure 3:
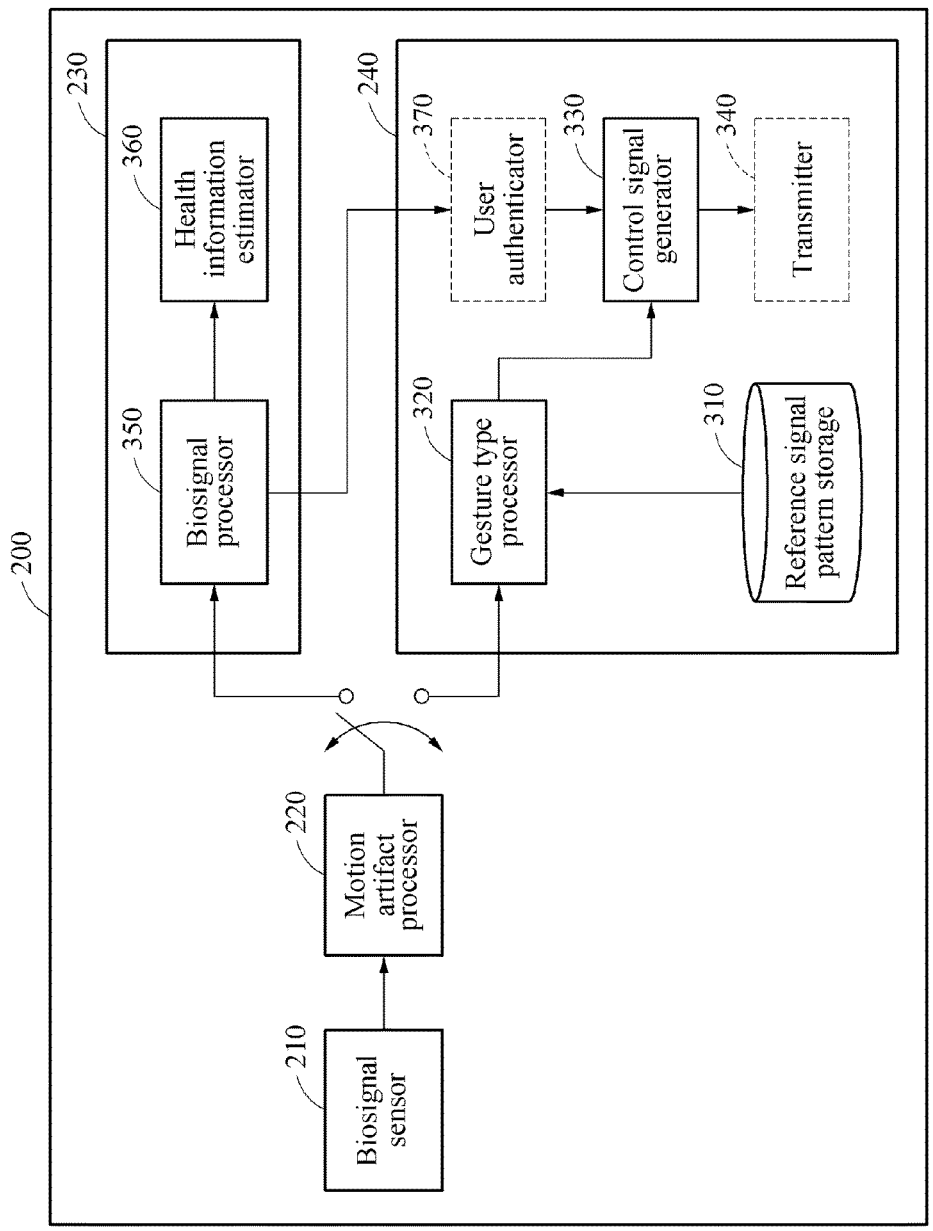

A detailed description of the health information processor 230 and the gesture recognition processor 240 will be provided with reference to FIG. 3. As described above, during the ordinary times when a user is not making intentional gestures, the wearable device 200 may determine health information of a user based on a biosignal measured by the biosignal sensor 210. When the user performs an intentional gesture to initiate a function of a target device, the wearable device 200 may analyze a signal pattern of a motion artifact occurring in an output signal of the biosignal sensor 210 and generate a control signal to initiate a function corresponding to the gesture performed by the user.

FIG. 3 is a diagram of an example of the wearable device 200 illustrated in FIG. 2.

Referring to FIG. 3, the health information processor 230 includes a biosignal processor 350 and a health information estimator 360. The biosignal processor 350 and health information estimator 360 may be implemented with one or more processors, circuits and memories. The biosignal processor 350 extracts a signal feature from a biosignal by processing the biosignal. The signal feature may include, for example, a maximum point, a minimum point, an inflection point, a maximum inclination point, and a minimum inclination point in a waveform of the biosignal, and a signal waveform area. However, a type of the signal feature is not limited to the aforementioned example. The health information estimator 360 estimates health information associated with health of a user based on the signal feature of the biosignal. The health information estimated by the health information estimator 360 is provided to the user through an output interface (not shown), for example, a display and a speaker, or stored in a separate storage (not shown). The health information estimator 360 also provides an alarm to the user in response to a determination that an abnormal health condition is occurring while a health condition of the user is being monitored.

The gesture recognition processor 240 includes a gesture type processor 320, a reference signal pattern storage 310, and a control signal generator 330. The gesture type processor 320 determines a type of a gesture performed by the user based on a signal pattern of a motion artifact and at least one reference signal pattern stored in the reference signal pattern storage 310. The control signal generator 330 generates a control signal corresponding to the determined type of the gesture. For example, the control signal may include a control signal to control a function of the wearable device 200 or a function of another device connected to the wearable device 200. A description of the gesture type processor 150 and the control signal generator 160 provided with reference to FIG. 1 is applicable to the gesture type processor 320 and the control signal generator 330, and thus a more detailed description will be omitted here. In an example, the gesture recognition processor 240 may further include a transmitter 340. The transmitter 340 wirelessly transmits the control signal to a target device to be controlled.

In this example, the gesture recognition processor 240 further includes a user authenticator 370. However, this features may not be present in another example, The user authenticator 370 performs user authentication to determine whether the user currently wearing the wearable device 200 is a registered user. In response to a determination that the signal feature of the measured biosignal corresponds to a signal feature of a biosignal of the registered user, the user authenticator 370 determines the user authentication to be successful. Conversely, in response to a determination that the signal feature of the biosignal does not correspond to the signal feature of the biosignal of the registered user, the user authenticator 370 determines the user authentication to be unsuccessful. In response to a successful user authentication, the user authenticator 370 controls the control signal to be normally output from the control signal generator 330. In response to an unsuccessful user authentication, the user authenticator 370 controls the control signal not to be output from the control signal generator 330.

Figure 4A:
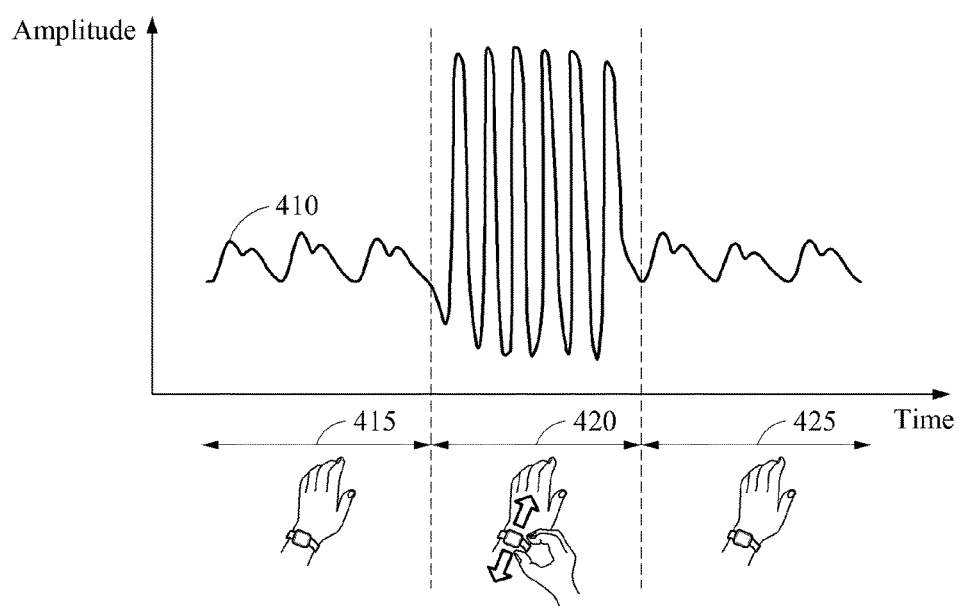
FIGS. 4A through 4C are diagrams illustrating examples of a change in an output signal of a biosignal sensor based on a gesture performed by a user.
Figure 4B:
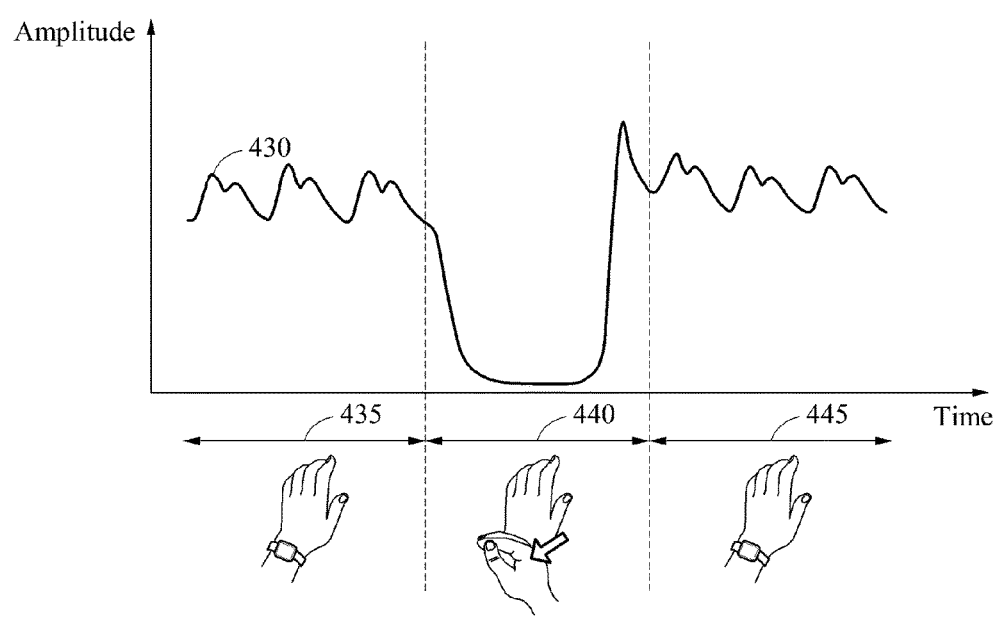
Figure 4C:
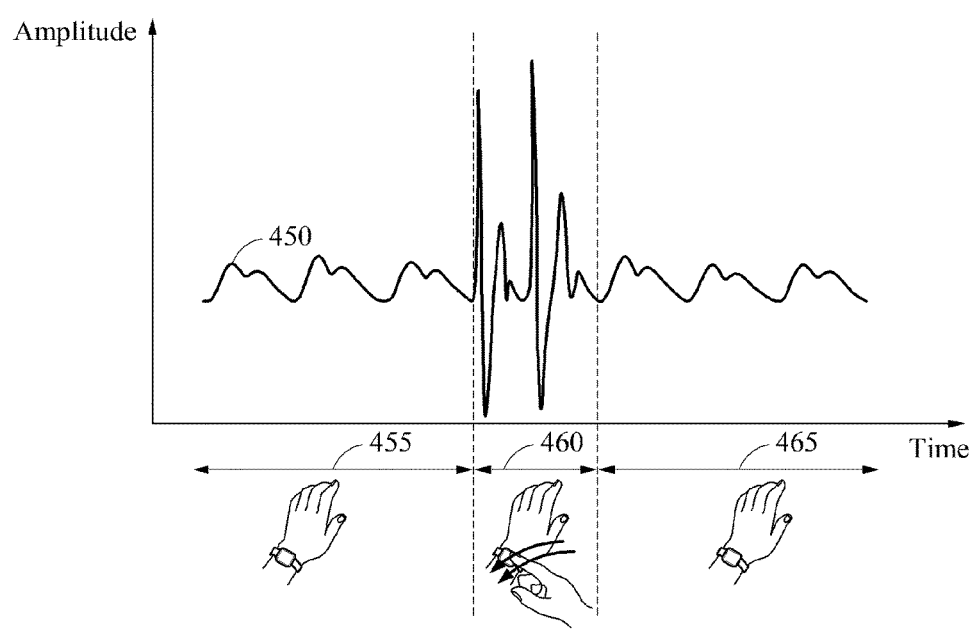

FIGS. 4A through 4C are diagrams illustrating examples of output signals of a biosignal sensor based on a gesture performed by a user. In the examples illustrated in FIGS. 4A through 4C, it is assumed that the biosignal sensor configured to measure a PPG signal from a wrist portion of a user is included in a wrist-worn watch-type wearable device, and a type of a pre-registered gesture includes a first gesture, a second gesture, and a third gesture.

FIG. 4A provides an example of an output signal of the biosignal sensor that illustrates a change in amplitude in the output signal based on the first gesture performed by the user. The first gesture involves holding the wearable device and shaking the wearable device from left to right or up and down the wrist. FIG. 4A illustrates an example of a waveform 410 of the output signal obtained from the biosignal sensor. During a first time interval 415 corresponding to a time frame when no motion artifacts are detected, a PPG signal is measured by the biosignal sensor. In response to the user performing the first gesture during a second time interval 420 to initiate a function of a target device, a motion artifact having a form in which an amplitude of the output signal fluctuates greatly occurs in the waveform 410 of the output signal. During a third time interval 425 after the first gesture is terminated, the PPG signal measured by the biosignal sensor occurs again in the waveform 410 of the output signal.

FIG. 4B illustrates an example of an output signal of the biosignal sensor when the second gesture is performed by a user by pressing the wearable device with the other hand by applying a downward force on the wearable device. Referring to FIG. 4B, an example of a waveform 430 of the output signal generated by the biosignal sensor is illustrated. During a first time interval 435 illustrated in FIG. 4B, a PPG signal is measured. During a second time interval 440, the user performs the second gesture. A motion artifact having a form in which a signal amplitude value of the output signal of the biosignal sensor is maintained under a small threshold value until the second gesture is terminated occurs. During a third time interval 445 illustrated in FIG. 4B, after the second gesture is terminated, the PPG signal occurs again in the waveform 430 of the output signal.

FIG. 4C illustrates an example of an output signal of the biosignal sensor generated when the third gesture is performed by the user by tapping twice an area in the vicinity of the wearable device with a finger. Referring to FIG. 4C, a waveform 450 of the output signal of the biosignal sensor is illustrated. During a first time interval 455 illustrated in FIG. 4C, a PPG signal is measured. During a second time interval 460 in which the user performs the third gesture, a motion artifact having a form in which an amplitude greatly fluctuates twice occurs. During a third time interval 465 after the third gesture is terminated, the PPG signal occurs again in the waveform 450 of the output signal.

In the examples illustrated in FIGS. 4A through 4C, the wearable device determines whether a motion artifact occurs in an output signal of the biosignal sensor, and estimates health information of the user based on a PPG signal when the motion artifact does not occur. When a motion artifact is detected in an output signal of the biosignal sensor, the wearable device determines a type of a gesture performed by the user based on a signal pattern of the motion artifact, and generates a control signal to perform a function corresponding to the gesture performed by the user. A signal pattern of a motion artifact may vary depending on a gesture performed by a user, and a type of a gesture performed by a user may be determined by identifying a signal pattern of a motion artifact based on each type of a gesture performed by the user.

A type of a gesture performed by a user is not limited to the examples illustrated in FIGS. 4A through 4C, and thus various changes and modifications may be made.

FIGS. 5A through 5D are diagrams illustrating examples of methods of sending a control command to initiate a function based on a gesture performed by a user. In the examples illustrated in FIGS. 5A through 5D, it is assumed that a corresponding function is initiated based on the first gesture, the second gesture, and the third gesture described with reference to FIGS. 4A through 4C.

Figure 5A:
FIGS. 5A through 5D are diagrams illustrating examples of controlling a function based on a gesture performed by a user.

FIG. 5A illustrates an example of a method of sending a control command for a function in response to a target device to be controlled being a wearable device. Referring to FIG. 5A, in response to recognizing a first gesture 510 being performed by the user by holding the wearable device and shaking the wearable device from left to right, a function of switching to a home screen is performed. In response to recognizing a second gesture 520 being performed by the user by pressing the wearable device with the other hand by applying a downward force, a toggle function of turning on or off the wearable device is performed. In response to recognizing a third gesture 530 being performed by the user by tapping twice an area in the vicinity of the wearable device with a finger, a frequently used application of the wearable device or an application pre-registered by the user is executed.

Figure 5B:
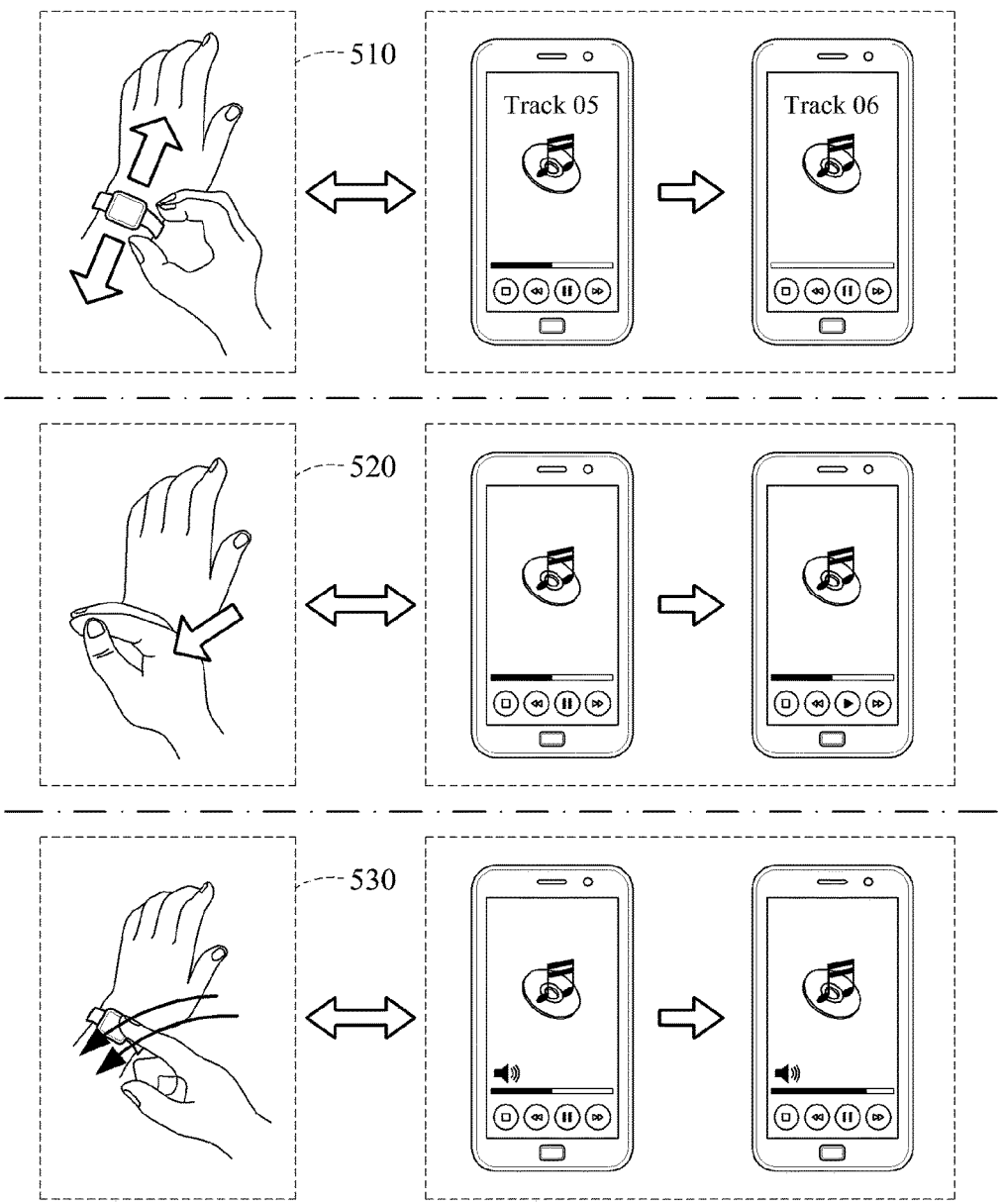

FIG. 5B illustrates an example of a method of generating a control command for a function when a target device to be controlled is a smartphone in which a music application is currently being executed. Referring to FIG. 5B, when the first gesture 510 is recognized, a function of playing a next song is performed in the music application. When the second gesture 520 is recognized, a toggle function of pausing and re-playing a song currently playing is performed. When the third gesture 530 is recognized, a function of turning up or down an audio volume in the music application is performed. According to these examples, the user may manipulate a function of an application being executed in the smartphone through intuitive gesture recognition, in lieu of direct manipulation made by a touch input to the application. Thus, user convenience may be improved.

Figure 5C:
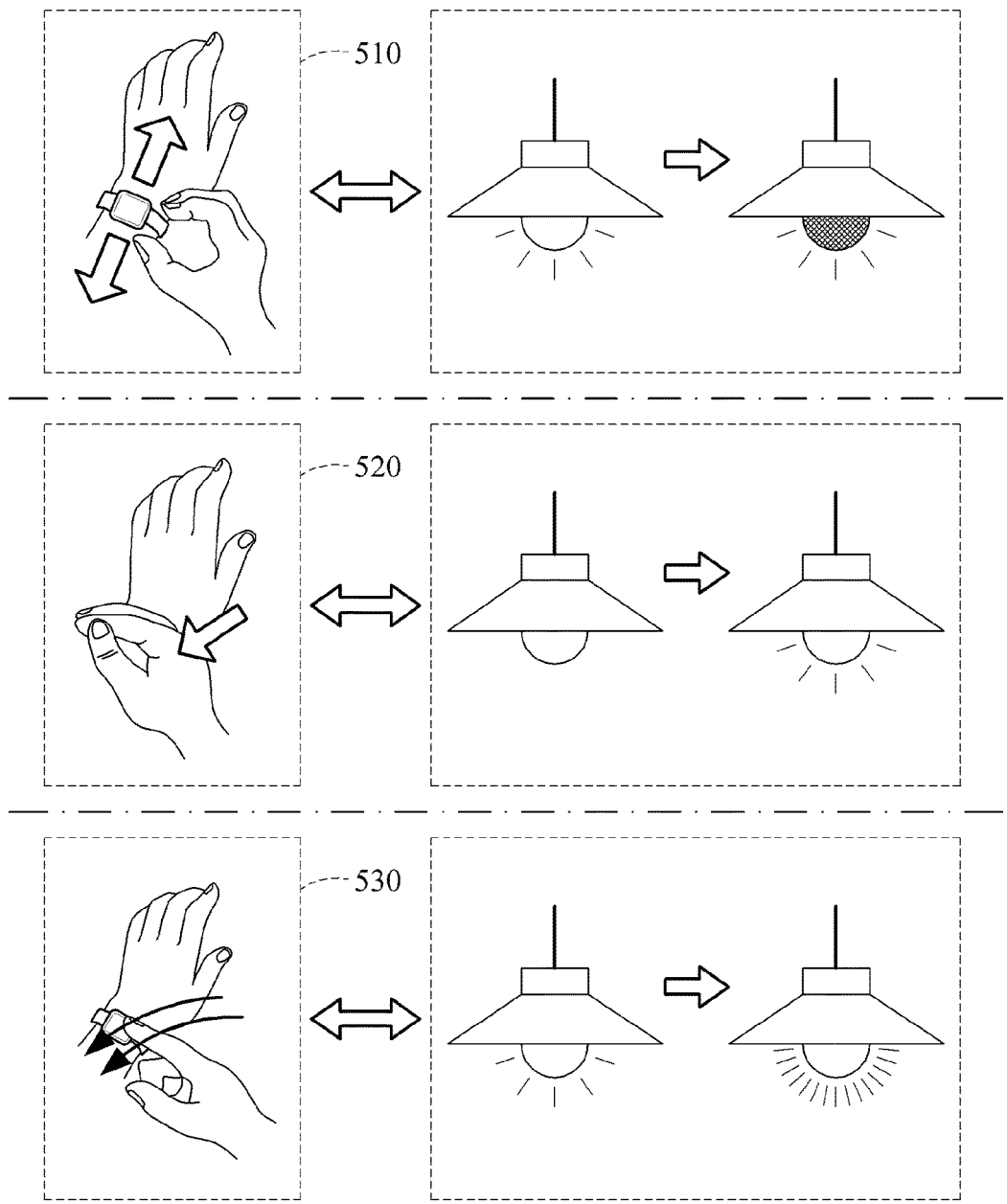

FIG. 5C illustrates an example of a method of controlling a function when a target device to be controlled is a smart lighting apparatus among Internet of things (IoT). Referring to FIG. 5C, in response to recognizing the first gesture 510, a function of the smart lighting apparatus, for example, a function of changing a color of light, is performed. In response to recognizing the second gesture 520, a function of turning on or off the smart lighting apparatus is performed. In response to recognizing the third gesture 530, a function of increasing or decreasing brightness of the smart lighting apparatus is performed. The user may control a function of another device present around the user or a wearable device worn on the user more conveniently through gesture recognition using the wearable device.

Figure 5D:
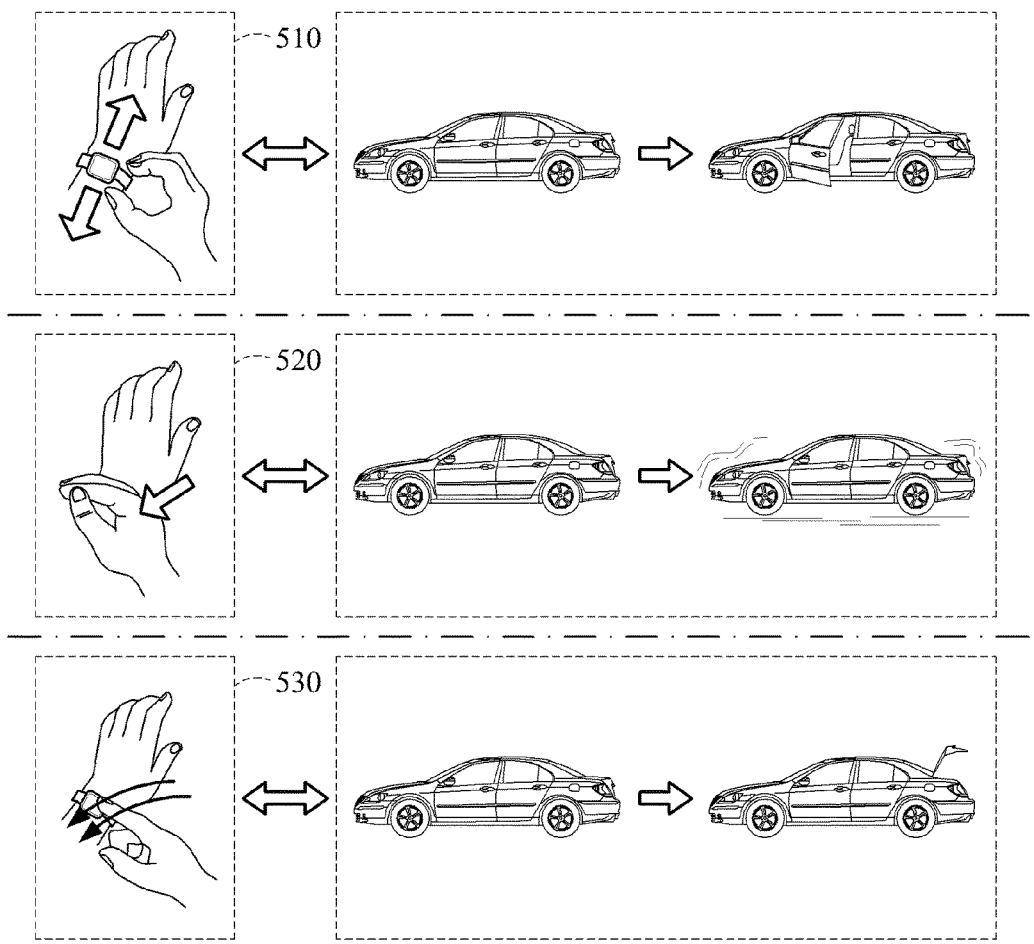

FIG. 5D illustrates an example of a method of controlling a function when a target device to be controlled is a smart vehicle. Referring to FIG. 5D, when the first gesture 510 is recognized, a function of opening a door of the smart vehicle being in a stationary state in which the smart vehicle is not travelling is performed. In response to recognizing the second gesture 520, a function of starting up the smart vehicle or a function of activating a door lock system is performed. In response to recognizing the third gesture 530, a function of opening a truck of the smart vehicle in the stationary state is performed. In an example, a biosignal-based user authentication may be performed before controlling a function. For example, the user authentication may be performed to determine whether a user wearing a wearable device is a registered user based on a biosignal of the user measured by a biosignal sensor. In response to a successful user authentication, the function may be controlled by recognizing a gesture performed by the user. In such an example, gesture recognition based on a signal pattern of a motion artifact may be performed prior to the user authentication or subsequent to the user authentication.

In the examples of FIGS. 5A through 5D, a control signal generated in response to recognizing a gesture performed by the user may be wirelessly transmitted to the smartphone, the smart lighting apparatus, the smart vehicle and the like. The control signal may be directly transmitted from the wearable device to such a target device to be controlled, or transmitted to the target device via another device connected to the wearable device. For example, the control signal may be transmitted by a smart phone connected to the wearable device. The wearable device and the target device may be connected to each other through various communication methods. For example, the wearable device and the target device may be connected to each other through a Wi-Fi method, a near-field communication (NFC) method, a second generation or third generation cellular communication system, a long-term evolution (LTE) method, a Bluetooth method and the like. The control signal may be transmitted from the wearable device to the target device based on the communication method.

A type of a gesture performed by a user and a type of a function to be controlled are not limited to the examples illustrated in FIGS. 5A through 5D, and thus various changes and modifications may be made.

FIG. 6 is a flowchart illustrating an example of a gesture recognition method. Referring to FIG. 6, in operation 610, a gesture recognition apparatus detects a motion artifact from an output signal of a biosignal sensor. In operation 620, the gesture recognition apparatus determines whether a signal pattern of the detected motion artifact corresponds to a predefined reference signal pattern. In operation 630, in response to the signal pattern of the motion artifact being determined to correspond to the reference signal pattern, the gesture recognition apparatus generates a control signal to control a function corresponding to the reference signal pattern. The control signal is transferred to a target device that is to perform a function to be controlled, and the target device performs a function defined by the received control signal. In operation 640, when the target device is located separately from the gesture recognition apparatus, the gesture recognition apparatus transmits, selectively and wirelessly, the control signal to the target device.

A detailed description of the gesture recognition method described with reference to FIG. 6 is previously provided with reference to FIG. 1, and thus a more detailed description will be omitted here.

Figure 7:
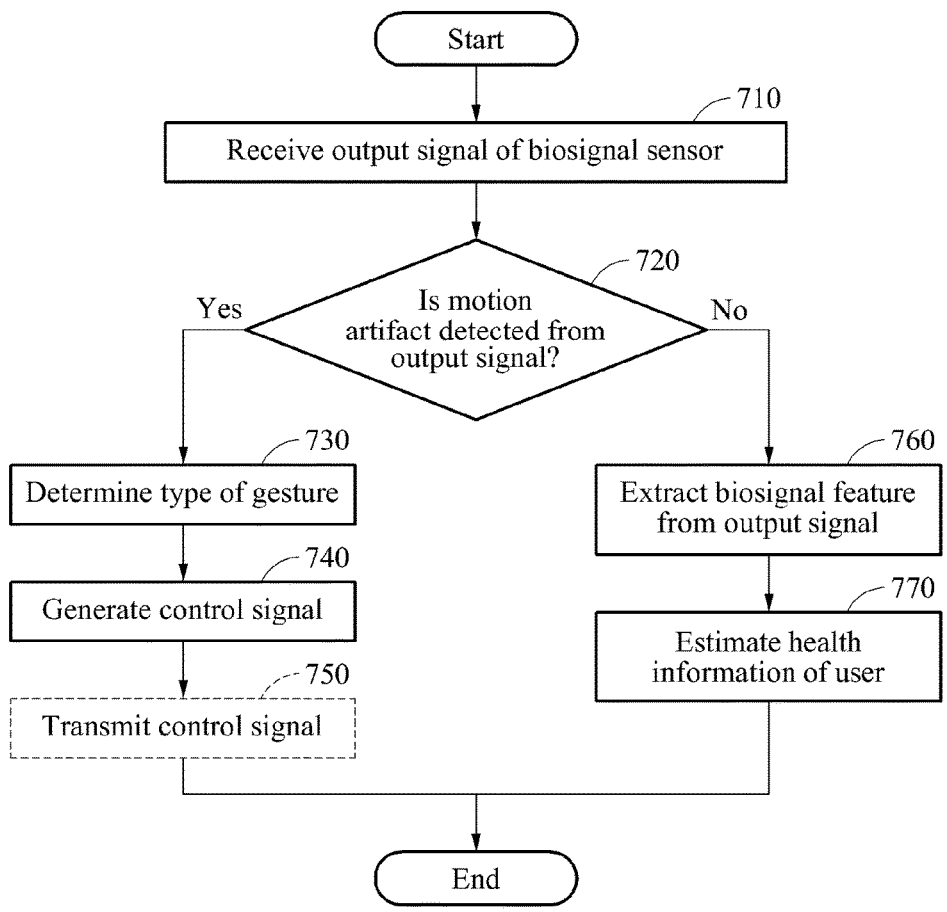
FIG. 7 is a flowchart illustrating an example of a process performed by a wearable device.

FIG. 7 is a flowchart illustrating an example of a process performed by a wearable device. Referring to FIG. 7, in operation 710, the wearable device receives an output signal of a biosignal sensor. In operation 720, the wearable device determines whether a motion artifact is detected from the output signal of the biosignal sensor. In operation 730, in response to the motion artifact being detected, the wearable device determines a type of a gesture performed by a user by comparing a signal pattern of the detected motion artifact to a pre-registered reference signal pattern. In operation 740, the wearable device generates a control signal to control a function corresponding to the determined type of the gesture, and the control signal is transferred to a target device that is to perform the function. In operation 750, in the event that the target device is located in a separate device, the wearable device transmits, selectively and wirelessly, the control signal to the target device.

In operation 760, in response to the motion artifact not being detected in operation 720, the wearable device extracts a biosignal feature from the output signal of the biosignal sensor. The biosignal feature refers to a feature of a biosignal to be measured by the biosignal sensor. In operation 770, the wearable device estimates health information of the user based on the extracted biosignal feature.

A detailed description of the process described with reference to FIG. 7 is previously provided with reference to FIGS. 2 and 3, and thus a more detailed description will be omitted here.

Figure 8:
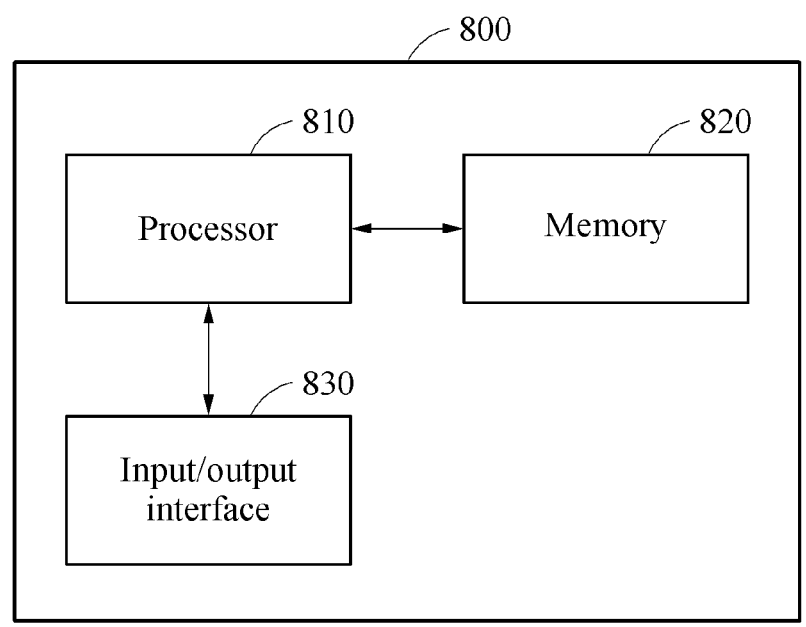
FIG. 8 is a diagram illustrating another example of a gesture recognition apparatus.

FIG. 8 is a diagram illustrating another example of a gesture recognition apparatus 800.

Referring to FIG. 8, the gesture recognition apparatus 800 includes at least one processor 810 and at least one memory 820.

The processor 810 performs at least one operation described with reference to FIGS. 1 through 7. For example, the processor 810 may detect a motion artifact from an output signal of a biosignal sensor, estimate a gesture performed by a user based on a signal pattern of the detected motion artifact, and generate a control signal to control a predefined function corresponding to the gesture performed by the user. The processor 810 may be configured as an array of logic gates, but it is obvious to one of ordinary skill in the art to which this disclosure pertains that the processor 810 may be configured as hardware of another form.

The memory 820 stores instructions to perform at least one operation described with reference to FIGS. 1 through 7, or stores data and results obtained during an operation of the gesture recognition apparatus 800. In some examples, the memory 820 may include a non-transitory computer-readable medium, for example, a high-speed random access memory and/or a nonvolatile computer-readable medium (e.g., at least one disk storage device, flash memory device, and other nonvolatile solid-state memory device).

In this example, the gesture recognition apparatus 800 further includes an input or output interface 830 such as a display, a keyboard, a touch screen, a microphone and the like, or a network communication interface to communicate with an external source. However, the present description is not limited thereto; in another example, the processor 810 may use an output signal of a biosignal sensor as an input. The input or output interface may receive an input from a user or output results from gesture recognition, for example, information on a function to be executed. The network communication interface may externally transmit the control signal generated by the processor 810.

The apparatuses, units, modules, devices, biosignal sensor, motion artifact processor, gesture type processor, control signal generator, transmitter, health information processor, user authenticator, reference signal pattern storage and other components illustrated in FIGS. 1, 2, 3, and 8 that perform the operations described herein with respect to FIGS. 6 and 7 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 6 and 7. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The examples of methods illustrated in FIGS. 6 and 7 that perform the operations described herein with respect to FIGS. 1 through 8 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of gesture recognition, the method comprising:
 using a processor to detect a motion artifact from an output signal of a biosignal sensor; and generating a control signal to control a function of a target device that corresponds to a reference signal pattern in response to a signal pattern of the detected motion artifact corresponding to the reference signal pattern.

2. The method of claim 1, wherein the generating of the control signal comprises:
determining a type of a gesture performed by a user based on the signal pattern of the motion artifact and at least one reference signal pattern stored in a memory; and
generating the control signal to operate the target device based on the determined type of the gesture.

3. The method of claim 1, wherein the motion artifact occurs by a physical pressure or a movement applied by a user to the biosignal sensor or an area in a vicinity of the biosignal sensor.

4. The method of claim 1, further comprising:
in response to the motion artifact not being detected from the output signal, estimating health information of a user based on a biosignal detected from the output signal.

5. The method of claim 1, wherein the generating of the control signal comprises:
performing a user authentication based on a biosignal detected from the output signal; and
generating the control signal in response to a successful user authentication.

6. The method of claim 1, wherein the generating of the control signal comprises:
determining presence or absence of the reference signal pattern corresponding to the signal pattern of the motion artifact among pre-registered reference signal patterns.

7. The method of claim 1, wherein the reference signal pattern is generated by determining a function type by a user selecting the function type and registering a signal pattern of a motion artifact corresponding to the determined function type.

8. The method of claim 1, wherein the biosignal sensor is comprised in a wearable device, and
the generating of the control signal to control the function of the target device comprises controlling a function of the wearable device or a function of another device connected to the wearable device.

9. The method of claim 8, wherein the other device is one of a mobile terminal, an Internet of things (IoT) device, and a smart vehicle.

10. The method of claim 1, wherein the detecting of the motion artifact comprises:
determining whether the motion artifact occurs based on a mean value of the output signal in a time interval.

11. The method of claim 1, further comprising:
wirelessly transmitting the control signal to a device performing the function.

12. The method of claim 1, wherein the biosignal sensor is configured to measure a biosignal comprising at least one of a photoplethysmogram (PPG) signal and an electrocardiogram (ECG) signal, the biosignal being associated with a health condition of a user.

13. A non-transitory computer-readable storage medium storing instructions that, when executed, cause computing hardware to perform the method of claim 1.

14. A gesture recognition apparatus comprising;
at least one processor; and
at least one memory configured to store instructions to be executed by the processor,
wherein the instructions, when executed, cause the processor to:
detect a motion artifact from an output signal of a biosignal sensor; and
generate a control signal to control a function of a target device corresponding to a reference signal pattern in response to a signal pattern of the detected motion artifact corresponding to the reference signal pattern.

15. The apparatus of claim 14, wherein the biosignal sensor is comprised in a wearable device, and
the generating of the control signal comprises:
generating the control signal to control a function of the wearable device or a function of another device connected to the wearable device.

16. The apparatus of claim 14, wherein the generating of the control signal comprises:
determining presence or absence of the reference signal pattern corresponding to the signal pattern of the motion artifact among pre-registered reference signal patterns.

17. A wearable device comprising:
a biosignal sensor configured to measure a biosignal; and
a motion artifact processor configured to determine whether a motion artifact is present in an output signal of the biosensor, and
in response to a determination that a motion artifact is present, initiate a gesture type processor to determine whether the motion artifact corresponds to a reference signal; and
in response to a determination that a motion artifact is not present, initiate a biosignal processor to process the output of the biosignal sensor to determine a health condition of a user.

18. The wearable device of claim 17, wherein the gesture type processor is configured to determine a type of a gesture performed by the user based on the signal pattern of the motion artifact and at least one reference signal pattern, and generate the control signal to control a function corresponding to the determined type of the gesture.

19. The wearable device of claim 17, wherein the gesture recognition processor is configured to perform a user authentication based on the biosignal and generate the control signal in response to a successful user authentication.

20. The wearable device of claim 17, further comprising:
a control signal generating circuit configured to generate a control signal based on the reference signal; and
a transmitter configured to transmit the control signal to a device located apart from the wearable device.

* * * * *